US011314314B2

(12) United States Patent
Okano et al.

(10) Patent No.: US 11,314,314 B2
(45) Date of Patent: Apr. 26, 2022

(54) HEAD-MOUNTED DISPLAY APPARATUS AND POWER SAVING CONTROL PROGRAM FOR HEAD-MOUNTED DISPLAY APPARATUS

(71) Applicant: SEIKO EPSON CORPORATION, Tokyo (JP)

(72) Inventors: Keiichi Okano, Chino (JP); Shinichi Kobayashi, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 17/161,671

(22) Filed: Jan. 29, 2021

(65) Prior Publication Data

US 2021/0240250 A1 Aug. 5, 2021

(30) Foreign Application Priority Data

Jan. 30, 2020 (JP) .............................. JP2020-013567

(51) Int. Cl.
*G06F 1/3234* (2019.01)
*G02B 27/01* (2006.01)
(Continued)

(52) U.S. Cl.
CPC .......... *G06F 1/3265* (2013.01); *A61B 5/6803* (2013.01); *G01C 19/00* (2013.01); *G01D 5/24* (2013.01); *G01P 15/18* (2013.01); *G02B 27/0172* (2013.01); *G02B 27/0176* (2013.01); *G06F 1/3287* (2013.01); *G06F 3/165* (2013.01); *G06T 7/97* (2017.01); *G09G 3/3208* (2013.01); *A61B 5/02438* (2013.01); *G02B 2027/0138* (2013.01); *G02B 2027/0178* (2013.01); *G09G 2330/022* (2013.01); *G09G 2330/023* (2013.01);
(Continued)

(58) Field of Classification Search
CPC ..................................................... G06F 1/3234
See application file for complete search history.

(56) References Cited

U.S. PATENT DOCUMENTS 10,055,887 B1 * 8/2018 Gil ....................... G02B 27/017
2009/0243970 A1 * 10/2009 Kato ................... G02B 27/0176
345/8

(Continued)

FOREIGN PATENT DOCUMENTS

JP 2015156610 8/2015

*Primary Examiner* — William Boddie
*Assistant Examiner* — Andrew B Schnirel
(74) *Attorney, Agent, or Firm* — JCIPRNET

(57) ABSTRACT

A head-mounted display apparatus includes an image display unit configured to display an image, a sound output unit configured to output a sound, a mounting state determination unit configured to determine a mounting state of the head-mounted display apparatus, and an image sound output control unit configured to turn ON/OFF display, and turn ON/OFF an output of a sound, based on the mounting state. The image sound output control unit is configured to turn ON display of an image and an output of a sound when the mounting state is the first state, turn OFF display of an image and turn ON an output of a sound when the mounting state is not the first state and is the second state, and turn OFF display of an image and an output of a sound when the mounting state is not the first state and is not the second state.

7 Claims, 16 Drawing Sheets

(51) Int. Cl.
*G06T 7/00* (2017.01)
*G06F 3/16* (2006.01)
*G01P 15/18* (2013.01)
*G01C 19/00* (2013.01)
*G01D 5/24* (2006.01)
*G06F 1/3287* (2019.01)
*A61B 5/00* (2006.01)
*G09G 3/3208* (2016.01)
*A61B 5/024* (2006.01)

(52) U.S. Cl.
CPC . *G09G 2330/026* (2013.01); *G09G 2330/027* (2013.01)

(56) References Cited

U.S. PATENT DOCUMENTS

| | | | |
|---|---|---|---|
| 2015/0130711 A1* | 5/2015 | Lee | G02B 27/017 345/156 |
| 2016/0062457 A1* | 3/2016 | Kobayashi | G06F 1/163 345/156 |
| 2017/0045928 A1 | 2/2017 | Ishikawa et al. | |
| 2018/0176547 A1* | 6/2018 | Kobayashi | H04N 13/332 |

* cited by examiner

|  | FIRST STATE | NOT FIRST STATE | |
|---|---|---|---|
|  |  | SECOND STATE | NOT SECOND STATE |
|  | MOUNTING IN FRONT OF EYES | MOUNTING ON HEAD | NON-MOUNTING |
| IMAGE DISPLAY | ON | OFF | OFF |
| VOICE OUTPUT | ON | ON | OFF |

FIG. 9

| FLIP-UP ANGLE | 0° ~15° | 15° ~45° | 45° ~90° | REMOVED |
|---|---|---|---|---|
| IMAGE DISPLAY | ON | ON (ONLY IN LOWER PORTION) | OFF | OFF |
| VOICE OUTPUT | ON | ON | ON | OFF |

FIG. 16

HEAD-MOUNTED DISPLAY APPARATUS AND POWER SAVING CONTROL PROGRAM FOR HEAD-MOUNTED DISPLAY APPARATUS

The present application is based on, and claims priority from JP Application Serial Number 2020-013567, filed Jan. 30, 2020, the disclosure of which is hereby incorporated by reference herein in its entirety.

BACKGROUND

1. Technical Field

The present disclosure relates to a head-mounted display apparatus and a power saving control program for a head-mounted display apparatus.

2. Related Art

JP-A-2015-156610 discloses an electronic apparatus that includes a wearable optical device. The electronic apparatus determines whether a state is at least any of a first state where the wearable optical device is mounted and usable and a second state where the wearable optical device is not used, controls a power supply state, based on the determination result, and achieves power saving.

However, in the electronic apparatus in JP-A-2015-156610, a state is determined as the second state when the wearable optical device is mounted or carried in an unusable state. Thus, for example, there is a problem that a state where the wearable optical device is mounted on a head of a user and a state where the wearable optical device is removed from a body and is carried may be determined as the same state.

SUMMARY

According to an aspect of the present disclosure, a head-mounted display apparatus is provided. The head-mounted display apparatus includes an image display unit configured to display an image, a sound output unit configured to output a sound, a mounting state determination unit configured to determine a mounting state of the head-mounted display apparatus, and an image sound output control unit configured to turn ON/OFF display of an image by the image display unit, and turn ON/OFF an output of a sound by the sound output unit, based on the mounting state, where the mounting state determination unit determines whether the mounting state is a first state where the head-mounted display apparatus is mounted in a position in which an image is visually recognizable, and determines whether the mounting state is a second state where the head-mounted display apparatus is mounted on a head, and the image sound output control unit is configured to turn ON display of an image and an output of a sound when the mounting state is the first state, turn OFF display of an image and turn ON an output of a sound when the mounting state is not the first state and is the second state, and turn OFF display of an image and an output of a sound when the mounting state is not the first state and is not the second state.

BRIEF DESCRIPTION OF THE DRAWINGS

FIG. 9 is an explanatory diagram illustrating a relationship between a mounting state of the HMD and ON/OFF of display of an image and a sound output of the HMD.

FIG. 16 is an explanatory diagram illustrating a relationship between a mounting state of an HMD in the fifth exemplary embodiment and ON/OFF of display of an image and a sound output of the HMD.

DESCRIPTION OF EXEMPLARY EMBODIMENTS

First Exemplary Embodiment

Figure 1:
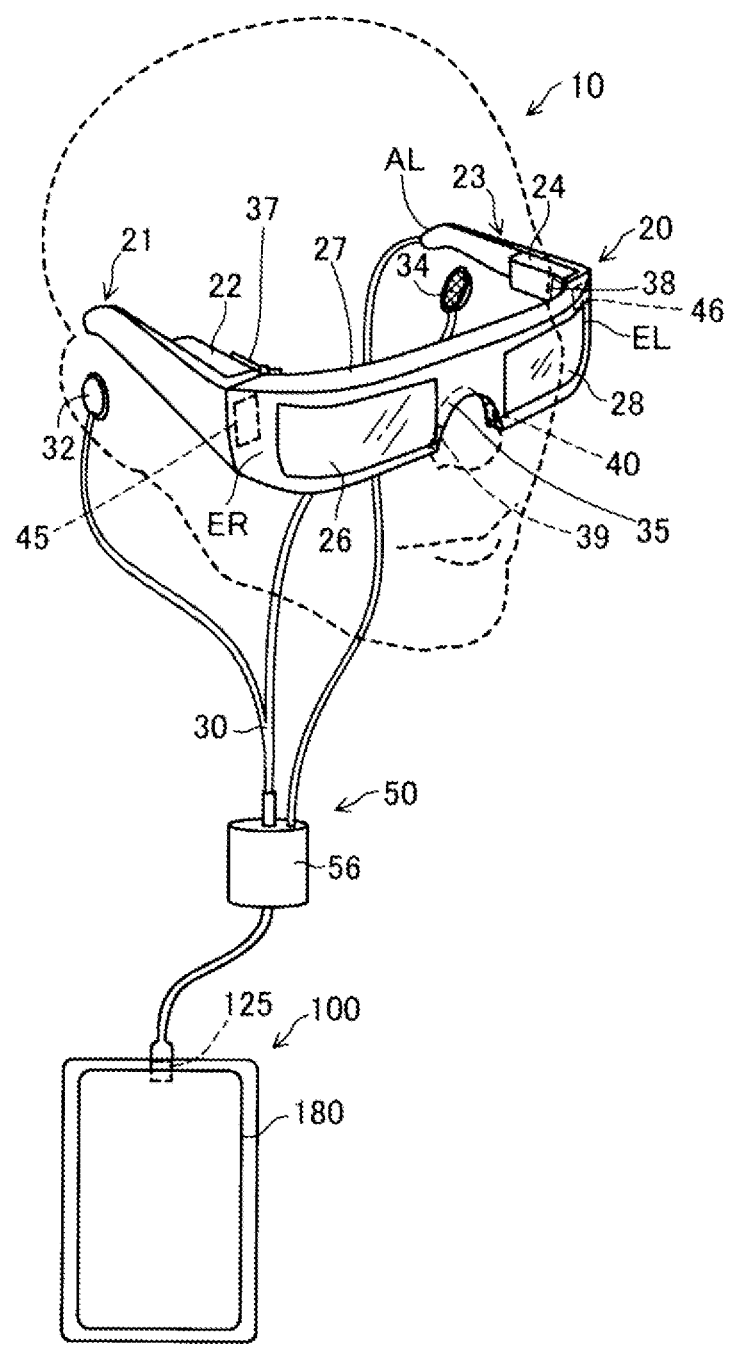
FIG. 1 is an explanatory diagram illustrating a head-mounted display apparatus according to a first exemplary embodiment.

FIG. 1 is an explanatory diagram of a head-mounted display apparatus 10 according to a first exemplary embodiment. The head-mounted display apparatus 10 is a display apparatus to be mounted on a head of the user and is also referred to as a head-mounted display (HMD). Hereinafter, the head-mounted display apparatus 10 is also referred to as an HMD 10. The HMD 10 is a see-through (transmission-type) head-mounted display apparatus that provides an image appearing in an outside scenery visually recognized through glasses. The HMD 10 includes an image display unit 20 and a control device (controller) 100 configured to control the image display unit 20.

The image display unit 20 is a head-mounted body to be mounted on the head of the user and has an eyeglasses-like shape. The image display unit 20 includes a support body including a right holding portion 21, a left holding portion 23, and a front frame 27 and further includes, on the support body, a right display unit 22, a left display unit 24, a right light-guiding plate 26, and a left light-guiding plate 28.

The right holding portion 21 and the left holding portion 23 are each coupled to the front frame 27 by hinges 37 and 38 such that the right holding portion 21 and the left holding portion 23 can be open and closed. The right holding portion 21 and the left holding portion 23 extend rearward from ends of the front frame 27 to hold the image display unit 20 on the head of the user in a manner similar to the temples of a pair of eyeglasses. Here, one of both the ends of the front frame 27 located on the right side of the user in a mounting state of the image display unit 20 is referred to as an end ER, and the other end located on the left side of the user in the mounting state is referred to as an end EL. The right holding portion 21 is provided to extend from the end ER of the front frame 27 to a position corresponding to the right temple of the user in the mounting state of the image display unit 20. The left holding portion 23 is provided to extend from the end EL of the front frame 27 to a position corresponding to the left temple of the user in the mounting state of the image display unit 20.

Pressure sensors 45 and 46 are each provided on the hinge portion between the right holding portion 21 and the left holding portion 23, and the front frame 27. A width of the front frame 27 is formed narrower than a width of the head, and thus, when the HMD 10 is mounted on a head of the user, the right holding portion 21 and the left holding portion 23 are widened and pressure applied to the pressure sensors 45 and 46 increases. Whether or not the HMD 10 is mounted on the head of the user can be determined by detecting the pressure.

The right light-guiding plate 26 and the left light-guiding plate 28 are provided in the front frame 27. The right light-guiding plate 26 is located in front of the right eye of the user in the mounting state of the image display unit 20 to allow the right eye to visually recognize an image. The left light-guiding plate 28 is located in front of the left eye of the user in the mounting state of the image display unit 20 to allow the left eye to visually recognize an image. In other words, the front frame 27 has a shape coupling an end of the right light-guiding plate 26 and an end of the left light-guiding plate 28 to each other. The coupling position corresponds to a position between eyebrows of the user in the mounting state of the image display unit 20.

The front frame 27 includes a nose pad 35 that is provided in the coupling position between the right light-guiding plate 26 and the left light-guiding plate 28, and that is in contact with a nose of the user in the mounting state of the image display unit 20. The nose pad 35, the right holding portion 21, and the left holding portion 23 allow the image display unit 20 to be held on the head of the user. The nose pad 35 is provided with nose pad sensors 39 and 40 configured to detect whether the HMD 10 is in contact with the nose of the user. The nose pad sensors 39 and 40 are a capacitance touch sensor, for example. As the nose pad sensors 39 and 40, a pulse wave sensor configured to detect a pulse wave of the nasal artery may be used.

The right display unit 22 is configured to display an image on the right light-guiding plate 26. The right display unit 22 is provided on the right holding portion 21 and located adjacent to the right temple of the user in the mounting state of the image display unit 20. The left display unit 24 is configured to display an image on the left light-guiding plate 28. The left display unit 24 is provided on the left holding portion 23 and located adjacent to the left temple of the user in the mounting state of the image display unit 20. Note that the right display unit 22 and the left display unit 24 are also collectively referred to as a "display driving unit".

The right light-guiding plate 26 and the left light-guiding plate 28 are optical parts (e.g., prisms) formed of a light transmission-type resin or the like, and are configured to guide imaging light output by the right display unit 22 and the left display unit 24 to the eyes of the user.

The control device 100 and the image display unit 20 are coupled to each other with a coupling cable 50. The coupling cable 50 is detachably coupled to a conductive connector 125 provided in the control device 100 and is coupled from a tip AL of the left holding portion 23 to various circuits inside the image display unit 20. The coupling cable 50 includes a metal cable or an optical fiber cable through which digital data is transmitted. The coupling cable 50 may further include a metal cable through which analog data is transmitted. A conductive connector 56 is provided in the middle of the coupling cable 50.

The conductive connector 56 is a jack to which a stereo mini-plug is coupled. The conductive connector 56 and the control device 100 are coupled to each other with, for example, a line through which an analog sound signal is transmitted. In the example illustrated in FIG. 1, the conductive connector 56 is coupled to a headset 30 including a right earphone 32 and a left earphone 34 constituting a stereo headphone as a sound output unit configured to output a sound.

The control device 100 is a device for controlling the HMD 10 (particularly, the image display unit 20). The control device 100 also functions as a supply device configured to supply an image and a sound. The HMD 10 receives a supply of an image and a sound from the control device 100, displays the image on the image display unit 20, and outputs the sound to the right earphone 32 and the left earphone 34. The control device 100 includes the conductive connector 125 and a touch panel 180. The touch panel 180 is configured to detect a touch operation from the user and output a signal corresponding to a detection content. The control device 100 controls the HMD 10 according to the signal. Any of various touch panels, such as an electrostatic-type touch panel, a pressure detection-type touch panel, and an optical touch panel, may be adopted as the touch panel 180. An internal configuration of the control device 100 will be described later.

Figure 2:
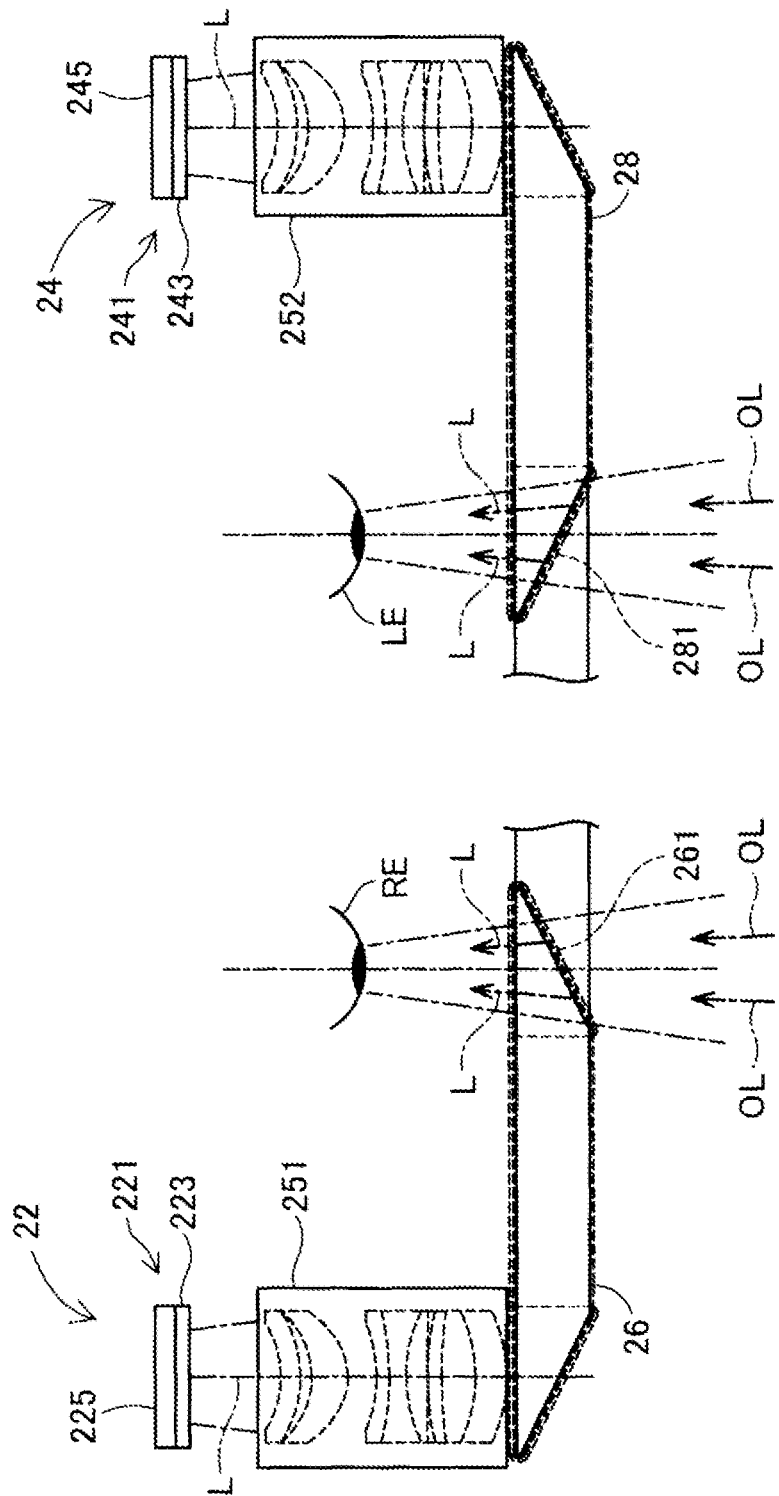
FIG. 2 is a plan view illustrating a configuration of a main part of an optical system included in an image display unit.

FIG. 2 is a plan view illustrating a main part of a configuration of an optical system included in the image display unit 20. For convenience of description, FIG. 2 illustrates right eye RE and left eye LE of the user. As illustrated in FIG. 2, the right display unit 22 and the left display unit 24 are arranged symmetrically on the right- and left-hand sides.

As a configuration in which the right eye RE is caused to visually recognize an image, the right display unit 22 includes an organic light emitting diode (OLED) unit 221 that is an organic EL and a right optical system 251. The OLED unit 221 is configured to emit imaging light L. The right optical unit 251 includes a lens group and the like, and is configured to guide, to the right light-guiding plate 26, the imaging light L emitted by the OLED unit 221.

The OLED unit 221 includes an OLED panel 223 and an OLED drive circuit 225 configured to drive the OLED panel 223. The OLED panel 223 is a light emission type display panel including light-emitting elements configured to emit red (R) color light, green (G) color light, and blue (B) color light, respectively, by organic electro-luminescence. The OLED panel 223 includes a plurality of pixels arranged in a matrix, each of the plurality of pixels including one element of R, one element of G, and one element of B.

The OLED drive circuit 225 is configured to select and power the light-emitting elements included in the OLED panel 223 to cause the light-emitting elements to emit light. The OLED drive circuit 225 is secured by bonding or the like onto a back surface of the OLED panel 223, i.e., a back side of a light-emitting surface. The OLED drive circuit 225 may include, for example, a semiconductor device configured to drive the OLED panel 223, and may be mounted onto a substrate secured to the back surface of the OLED panel 223. The OLED panel 223 may be configured to include light-emitting elements, arranged in a matrix, that emit white color light, and color filters, disposed over the light-emitting elements, that correspond to the R color, the G color, and the B color, respectively. The OLED panel 223 may have a WRGB configuration including light-emitting elements configured to emit white (W) color light, in addition to light-emitting elements configured to emit R color light, G color light, and B color light, respectively.

The right optical system 251 includes a collimate lens configured to collimate the imaging light L emitted from the OLED panel 223. The imaging light L collimated by the collimate lens enters the right light-guiding plate 26. In an optical path configured to guide light inside the right light-guiding plate 26, a plurality of reflective surfaces configured to reflect the imaging light L are formed. The imaging light L is reflected multiple times inside the right light-guiding plate 26 and then, is guided to the right eye RE side. In the right light-guiding plate 26, a half mirror 261 (reflective surface) located in front of the right eye RE is formed. The imaging light L reflected by the half mirror 261 is emitted from the right light-guiding plate 26 to the right eye RE. The imaging light L forms an image on the retina of the right eye RE to allow the user to visually recognize the image.

As a configuration in which the left eye LE is caused to visually recognize an image, the left display unit 24 includes an OLED unit 241 and a left optical system 252. The OLED unit 241 is configured to emit the imaging light L. The left optical system 252 includes a lens group and the like, and is configured to guide, to the left light-guiding plate 28, the imaging light L emitted by the OLED unit 241. The OLED unit 241 includes an OLED panel 243 and an OLED drive circuit 245 configured to drive the OLED panel 243. For further details, the OLED unit 241, the OLED panel 243, and the OLED drive circuit 245 are the same as the OLED unit 221, the OLED panel 223, and the OLED drive circuit 225, respectively. Note that, for further details, the left optical system 252 is the same as the right optical system 251.

The imaging light L reflected by the half mirror 261 and outside light OL passing through the right light-guiding plate 26 enter the right eye RE of the user. The imaging light L reflected by a half mirror 281 and the outside light OL passing through the left light-guiding plate 28 enter the left eye LE of the user. In this manner, the HMD 10 allows the imaging light L of the internally processed image and the outside light OL to enter the eyes of the user in an overlapped manner. As a result, the user views an outside scenery (real world) through the right light-guiding plate 26 and the left light-guiding plate 28 and also visually recognizes an image formed by the imaging light L overlapping the outside scenery.

Each of the half mirror 261 and the half mirror 281 is configured to reflect the imaging light L output by each of the right display unit 22 and the left display unit 24 and extract an image. The right optical system 251 and the right light-guiding plate 26 are also collectively referred to as a "right light-guiding unit" and the left optical system 252 and the left light-guiding plate 28 are also collectively referred to as a "left light-guiding unit". Configurations of the right light-guiding unit and the left light-guiding unit are not limited to the example described above, and can use any manner as long as the imaging light L forms an image in front of the eyes of the user. For example, diffraction gratings or translucent reflective films may be used for the right light-guiding unit and the left light-guiding unit.

Figure 3:
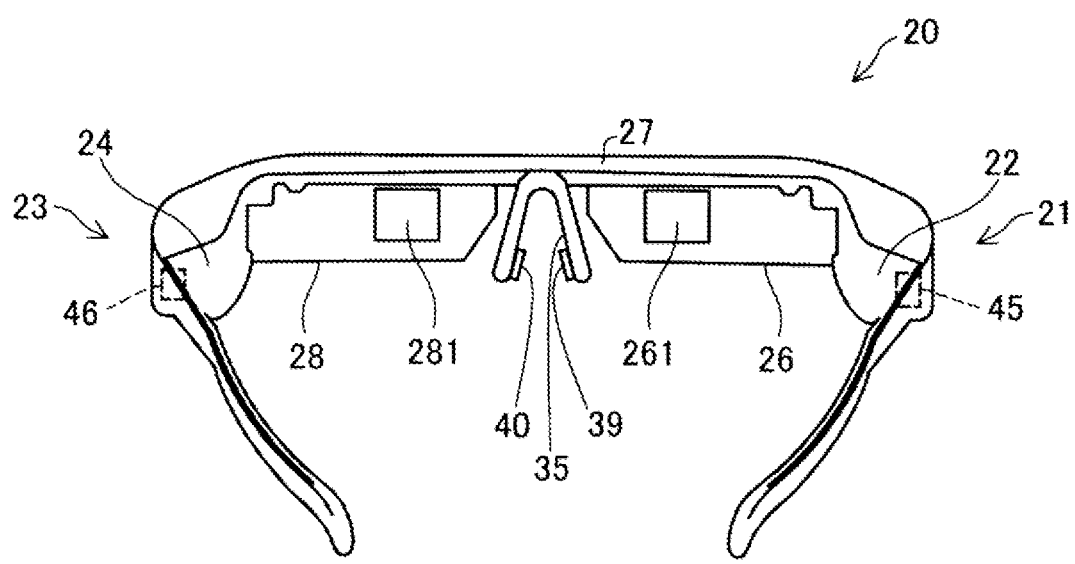
FIG. 3 is a diagram illustrating a configuration of a main part of the image display unit as viewed from a user.

FIG. 3 is a diagram illustrating a configuration of a main part of the image display unit 20 as viewed from the user. In FIG. 3, illustration of the coupling cable 50, the right earphone 32, the left earphone 34, and the like is omitted. In the state illustrated in FIG. 3, back sides of the right light-guiding plate 26 and the left light-guiding plate 28 can be visually recognized. The half mirror 261 configured to irradiate the imaging light L to the right eye RE, and the half mirror 281 configured to irradiate the imaging light L to the left eye LE can also be visually recognized as approximately square-shaped regions. The user visually recognizes an outside scenery through the entire areas of the right light-guiding plate 26 and the left light-guiding plate 28 including the half mirrors 261 and 281, and also visually recognizes rectangular display images in the positions of the half mirrors 261 and 281. Further, the pressure sensors 45 and 46 are each provided on the hinge portion between the right holding portion 21 and the left holding portion 23, and the front frame 27.

Figure 4:
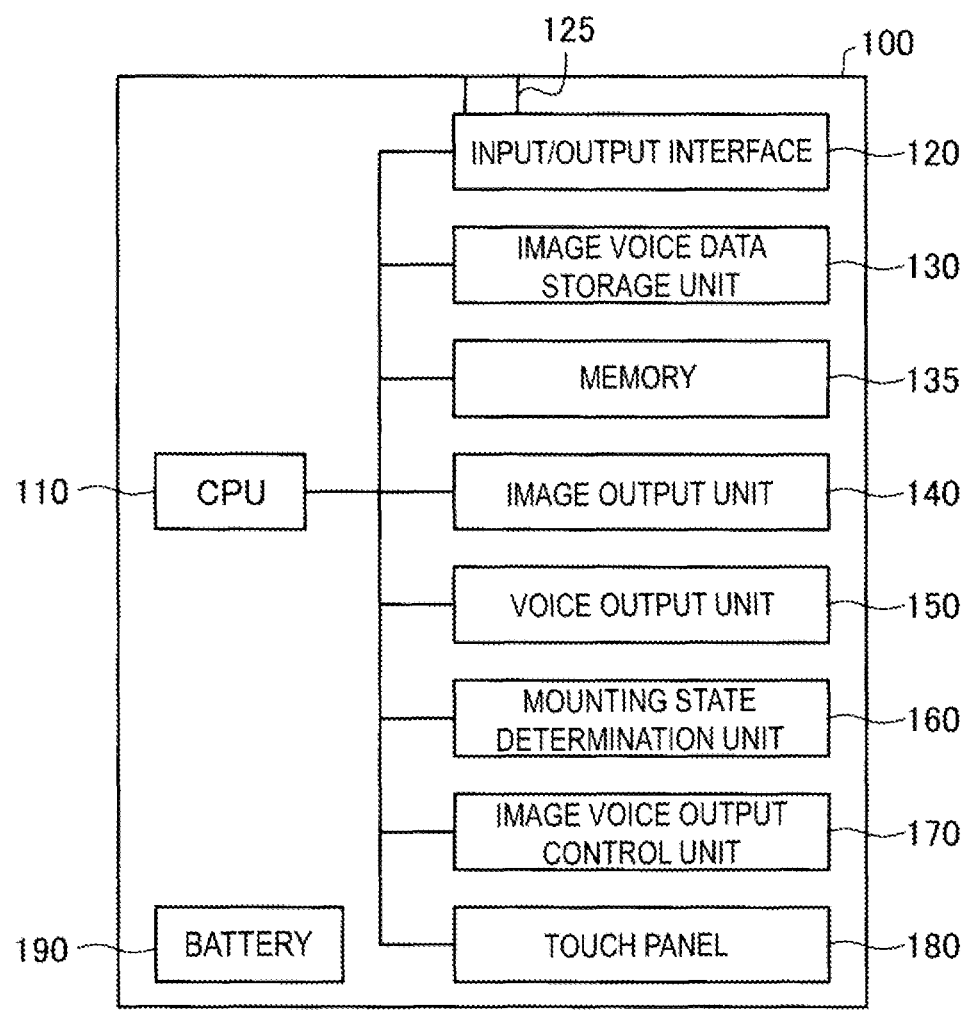
FIG. 4 is a block diagram illustrating a configuration of a control device.

FIG. 4 is a block diagram illustrating a configuration of the control device 100. The control device 100 includes a CPU 110, an input/output interface 120, an image sound data storage unit 130, a memory 135, an image output unit 140, a sound output unit 150, a mounting state determination unit 160, an image sound output control unit 170, a touch panel 180, and a battery 190. The input/output interface 120 includes the conductive connector 125, and the coupling cable 50 (FIG. 1) is inserted into the conductive connector 125. The image sound data storage unit 130 stores data about an image and a sound to be output to the HMD 10. The memory 135 stores a measurement value of various sensors of the HMD 10. The image output unit 140 outputs an image stored in the image sound data storage unit 130 to the image display unit 20 of the HMD 10. The sound output unit 150 outputs a sound stored in the image sound data storage unit 130 to the right earphone 32 and the left earphone 34 of the HMD 10. The mounting state determination unit 160 determines a mounting state of the HMD 10 on the user by using various sensors provided in the HMD 10 and an image captured by a camera 36. According to the mounting state of the HMD 10 on the user, the image sound output control unit 170 turns ON/OFF an output of an image from the image output unit 140 to the image display unit 20 of the HMD 10, and turns ON/OFF an output of a sound from the sound output unit 150 to the right earphone 32 and the left earphone 34 of the HMD 10. The mounting state determination unit 160 and the image sound output control unit 170 are computer programs and are executed by the CPU 110. The touch panel 180 is an input device to the control device 100 of the user, and is used to operate the HMD 10 by the user and select an image and a sound stored in the image sound data storage unit 130. Further, the touch panel 180 displays an image. The battery 190 is a power supply configured to supply power to the control device 100 and the HMD 10.

Figure 5:
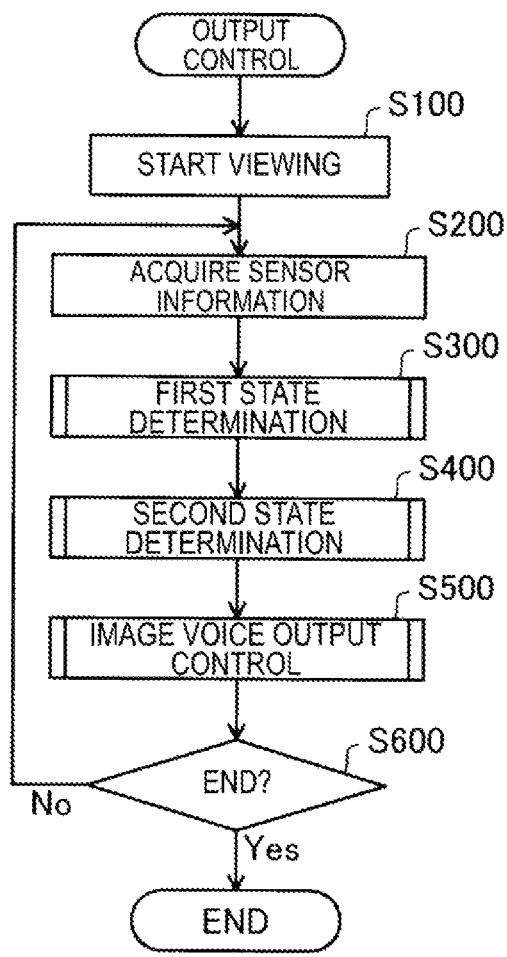
FIG. 5 is an output control flowchart for an image and a sound to an HMD performed by a CPU of the control device.

FIG. 5 is an output control flowchart for an image and a sound to the HMD 10 performed by the CPU 110 of the control device 100. In step S100, when the touch panel 180 of the control device 100 receives an instruction of a viewing start from the user, the CPU 110 causes the image output unit 140 and the sound output unit 150 to output an image and a sound to the HMD 10, respectively.

In step S200, the CPU 110 acquires information of the nose pad sensors 39 and 40 and the pressure sensors 45 and 46, and stores the information in the memory 135.

In step S300, the CPU 110 uses the information of the nose pad sensors 39 and 40, and determines whether a mounting state of the HMD 10 of the user is a first state. The first state refers to a state where the user wears the HMD 10 while the user can view an image.

In step S400, the CPU 110 uses the information of the pressure sensors 45 and 46, and determines whether the mounting state of the HMD 10 of the user is a second state. The second state refers to a state where the user wears the HMD 10 on the head of the user.

In step S500, the CPU 110 controls ON/OFF of an output of an image and a sound depending on whether the mounting state of the HMD 10 of the user is the first state, the second state, or neither the first state nor the second state.

In step S600, when the CPU 110 receives an instruction of discontinuance of viewing from the user, the CPU 110 terminates the processing, and, when the CPU 110 does not receive an instruction of discontinuance of viewing from the user, the CPU 110 returns the processing to step S200 and repeats the processing described above. The user instructs discontinuance of viewing by, for example, making an input to the touch panel 180.

Figure 6:
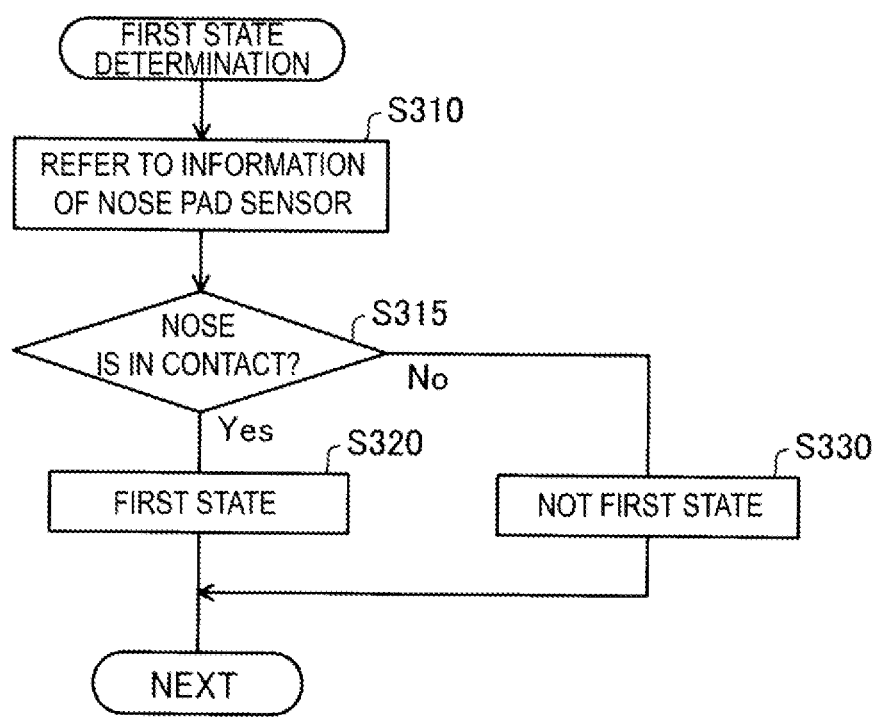
FIG. 6 is an example of a first state determination flowchart performed by the CPU in step S300 in FIG. 5.

FIG. 6 is an example of a first state determination flowchart performed by the CPU 110 in step S300 in FIG. 5. In step S310, the CPU 110 refers to, for determination, the output of the nose pad sensors 39 and 40 being acquired in step S200 in FIG. 5 and stored in the memory 135. In step S315, the CPU 110 determines whether the nose of the user is in contact with the nose pad sensors 39 and 40 by using the output of the nose pad sensors 39 and 40. When the nose of the user is in contact with the nose pad sensors 39 and 40, the CPU 110 transitions the processing to step S320, and determines that the mounting state of the HMD 10 is the first state. On the other hand, when the nose of the user is not in contact with the nose pad sensors 39 and 40, the CPU 110 transitions the processing to step S330, and determines that the mounting state of the HMD 10 is not the first state.

Figure 7:
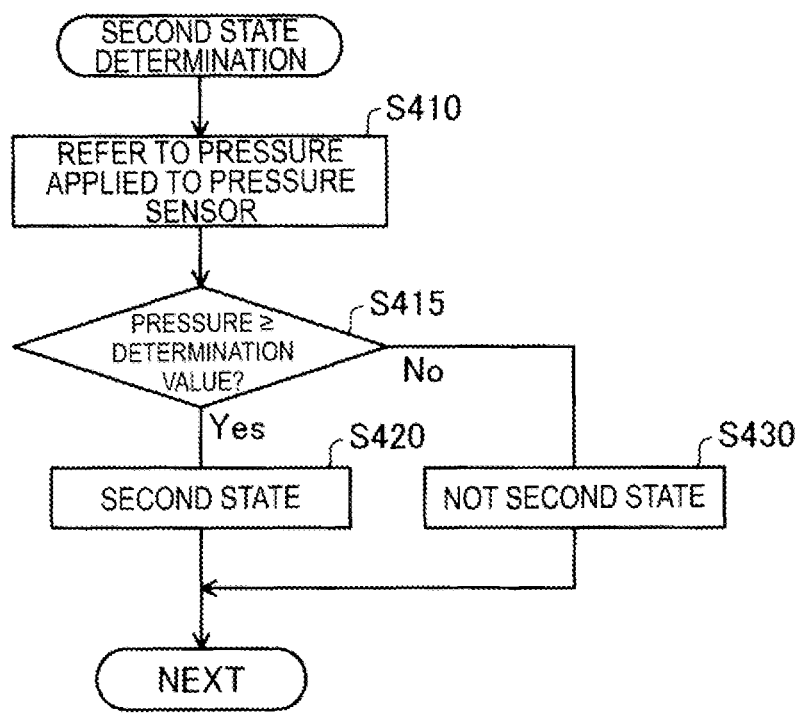
FIG. 7 is an example of a second state determination flowchart performed by the CPU in step S400 in FIG. 5.

FIG. 7 is an example of a second state determination flowchart performed by the CPU 110 in step S400 in FIG. 5. In step S410, the CPU 110 refers to, for determination, values of the pressure applied to the pressure sensors 45 and 46 being acquired in step S200 in FIG. 5 and stored in the memory 135. In step S415, the CPU 110 determines whether both of the values of the pressure applied to the pressure sensors 45 and 46 are equal to or greater than a predetermined determination value. When both of the values of the pressure applied to the pressure sensors 45 and 46 are equal to or greater than the determination value, the CPU 110 transitions the processing to step S420, and determines that the mounting state of the HMD 10 is the second state where the HMD 10 is mounted on the head of the user. On the other hand, when at least one of the values of the pressure applied to the pressure sensors 45 and 46 is less than the determination value, the CPU 110 transitions the processing to step S430 in step S310, and determines that the mounting state of the HMD 10 is neither the first state nor the second state.

Figure 8:
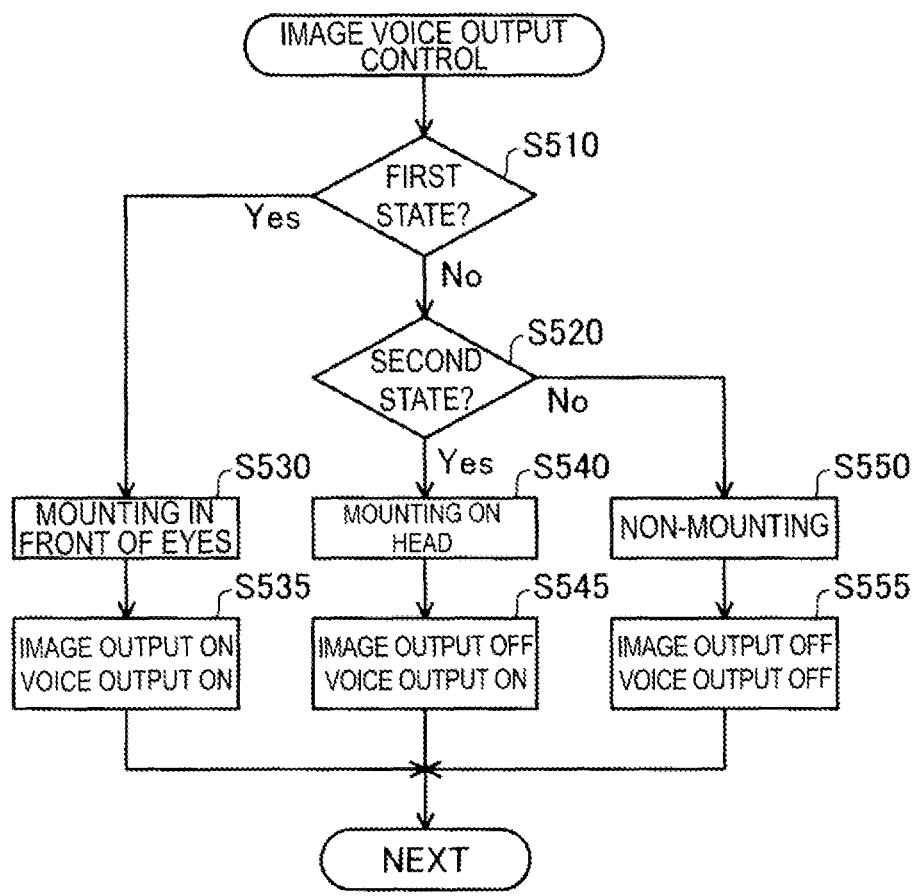
FIG. 8 is an ON/OFF control flowchart of an image sound output performed by the CPU in step S500 in FIG. 5.

FIG. 8 is an ON/OFF control flowchart of the image sound output performed by the CPU 110 in step S500 in FIG. 5. In step S510, when the CPU 110 determines that the mounting state of the HMD 10 is the first state, the CPU 110 transitions the processing to step S530, and, when the CPU 110 determines that the mounting state of the HMD 10 is not the first state, the CPU 110 transitions the processing to step S520. In step S520, when the CPU 110 determines that the mounting state of the HMD 10 is the second state, the CPU 110 transitions the processing to step S540, and, when the CPU 110 determines that the mounting state of the HMD 10 is not the second state, the CPU 110 transitions the processing to step S550.

In step S530, the CPU 110 determines that the user wears the HMD 10 in front of the eyes, and transitions the processing to step S535. In step S535, the CPU 110 causes the image sound output control unit 170 to turn ON an output of an image from the image output unit 140 to the image display unit 20 of the HMD 10, and causes the image sound output control unit 170 to turn ON an output of a sound from the sound output unit 150 to the HMD 10. In this way, when the output of the image from the image output unit 140 is ON, the HMD 10 maintains ON, and, when the output is OFF, the HMD 10 switches the output to ON. Further, when the output of the sound from the right earphone 32 and the left earphone 34 is ON, the HMD 10 maintains ON, and, when the output is OFF, the HMD 10 switches the output to ON.

In step S540, the CPU 110 determines that the user wears the HMD 10 on the head, and transitions the processing to step S545. In step S545, the CPU 110 causes the image sound output control unit 170 to turn OFF an output of an image from the image output unit 140 to the image display unit 20, and causes the image sound output control unit 170 to turn ON an output of a sound from the sound output unit 150 to the HMD 10. In this way, when the output of the image from the image output unit 140 is ON, the HMD 10 switches the output to OFF, and, when the output is OFF, the HMD 10 maintains OFF. Further, when the output of the sound from the right earphone 32 and the left earphone 34 is ON, the HMD 10 maintains ON, and, when the output is OFF, the HMD 10 switches the output to ON.

In step S550, the CPU 110 determines non-mounting where the user does not wear the HMD 10, and transitions the processing to step S555. In step S555, the CPU 110 causes the image sound output control unit 170 to turn OFF an output of an image from the image output unit 140 to the image display unit 20, and causes the image sound output control unit 170 to turn OFF an output of a sound from the sound output unit 150 to the HMD 10. In this way, when the output of the image from the image output unit 140 is ON, the HMD 10 switches the output to OFF, and, when the output is OFF, the HMD 10 maintains OFF. Further, when the output of the sound from the right earphone 32, the left earphone 34 is ON, the HMD 10 switches the output to OFF, and, when the output is OFF, the HMD 10 maintains OFF.

FIG. 9 is an explanatory diagram illustrating a relationship between a mounting state of the HMD 10 and ON/OFF of display of an image and a sound output of the HMD 10. When the mounting state of the HMD 10 is the first state, the image output is ON, but when the mounting state of the HMD 10 is not the first state, the image output is OFF. Further, when the mounting state of the HMD 10 is either the first state or the second state, the sound output is ON, but when the mounting state of the HMD 10 is neither the first state nor the second state, the sound output is OFF.

According to the first exemplary embodiment, the CPU 110 determines whether the mounting state is the first state where the HMD 10 is mounted in a first position in which an image is visually recognizable, and determines whether the mounting state is the second state where the HMD 10 is mounted in a second position in which an image is not visually recognizable. The CPU 110 is configured to turn ON display of an image and an output of a sound when the mounting state is the first state, turn OFF display of an image and turn ON an output of a sound when the mounting state is not the first state and is the second state, and turn OFF display of an image and an output of a sound when the mounting state is neither the first state nor the second state. In this way, although the user wears the HMD 10, when the user is not viewing an image, the CPU 110 turns OFF display of the image, and can thus reduce unnecessary power consumption of the battery 190.

According to the first exemplary embodiment, the CPU 110 determines whether the mounting state is the first state or is not the first state depending on whether the nose of the user is in contact with the nose pad sensors 39 and 40. In other words, when the nose is in contact with the nose pad sensors 39 and 40, the right light-guiding plate 26 is located in front of the right eye of the user and the left light-guiding plate 28 is located in front of the right eye of the user, and thus it can be determined that the user wears the HMD 10 in the first position in which an image is visually recognizable.

According to the first exemplary embodiment, the HMD 10 includes the front frame 27 configured to support the image display unit 20, the temples 21 and 23 provided so as to sandwich the front frame 27, the hinges 37 and 38 configured to couple the front frame 27 and the temples 21 and 23 in an openable and closable manner, and the pressure sensors 45 and 46 configured to detect pressure when the hinges 37 and 38 are open. The CPU 110 determines whether the mounting state of the HMD 10 is the second state or is not the second state by using a change in the pressure detected by the pressure sensors 45 and 46. In general, a spacing between the temples 21 and 23 is narrower than a width of the head. Thus, when the user wears the HMD 10 on the head, that is, in a case of the second state, the temples 21 and 23 are spread out and the pressure applied to the pressure sensors 45 and 46 increases. Therefore, the CPU 110 can easily determine whether the mounting state of the HMD 10 is the second state or is not the second state by using the pressure applied to the pressure sensors 45 and 46.

Second Exemplary Embodiment

Figure 10:
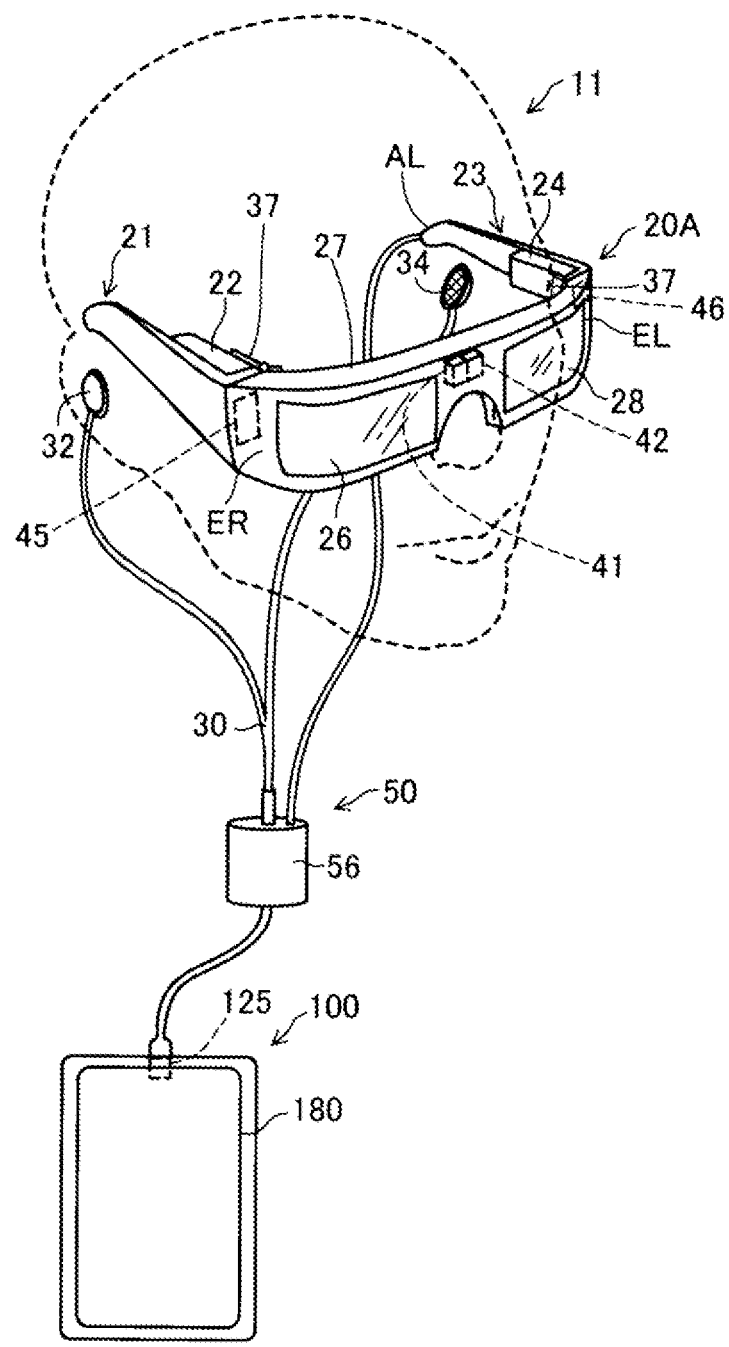
FIG. 10 is an explanatory diagram illustrating a head-mounted display apparatus according to a second exemplary embodiment.

FIG. 10 is an explanatory diagram illustrating a head-mounted display apparatus 11 (hereinafter referred to as an "HMD 11") according to a second exemplary embodiment. The HMD 10 in the first exemplary embodiment and the HMD 11 in the second exemplary embodiment are different in a sensor for detecting a mounting state of the HMD 11 being provided in an image display unit 20A, but other configurations are the same. Specifically, the HMD 11 does not include the nose pad sensors 39 and 40 and instead includes an acceleration sensor 41 and a gyro sensor 42. Hereinafter, the acceleration sensor 41 and the gyro sensor 42 for detecting a mounting state, and a control flow using these sensors will be described.

The image display unit 20A of the HMD 11 includes the acceleration sensor 41 and the gyro sensor 42 in a coupling portion of the right light-guiding plate 26 and the left light-guiding plate 28 of the front frame 27. The acceleration sensor 41 acquires acceleration in three directions with respect to the HMD 11. The gyro sensor 42 acquires an angular speed about three axes of the HMD 11. Note that, in the example in FIG. 10, the acceleration sensor 41 and the gyro sensor 42 are provided in the coupling portion of the right light-guiding plate 26 and the left light-guiding plate 28 of the front frame 27, but may be provided in another place of the HMD 11.

Figure 11:
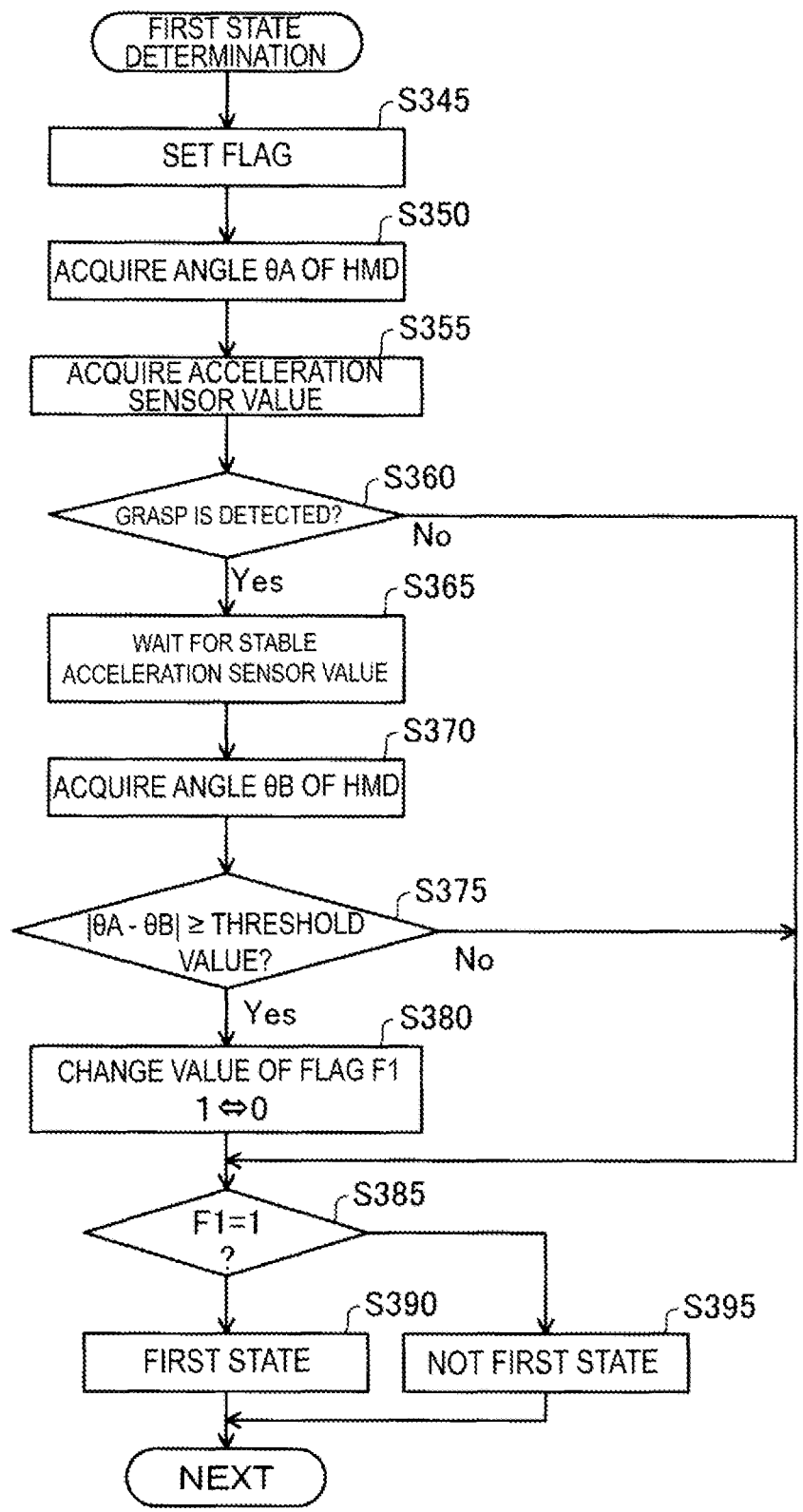
FIG. 11 is an example of a first state determination flowchart performed by the CPU in step S300 in FIG. 5 in the second exemplary embodiment.

FIG. 11 is an example of a first state determination flowchart performed by the CPU 110 in step S300 in FIG. 5 in the second exemplary embodiment. In step S345, the CPU 110 sets a flag. Specifically, immediately after the power of the HMD 11 is turned ON, "Please press start button of touch panel 180 of control device 100" is displayed on the image display unit 20 of the HMD 11 or the touch panel 180 of the control device 100 when a viewing state is entered, and, when the start button is pressed, the CPU 110 determines that the state is the first state and sets a flag F1 of the memory 135 to 1. Note that this step S345 is performed only once immediately after the user turns on the power of the HMD 11.

In step S350, the CPU 110 acquires a mounting angle θA of the HMD 11 by using the gyro sensor 42. In step S355, the CPU 110 acquires a value of the acceleration sensor 41.

In step S360, the CPU 110 determines whether the HMD 11 is grasped by the user. The CPU 110 determines that the HMD 11 is grasped by the user when the value of the acceleration sensor 41 is greater than a predetermined value. When the HMD 11 is grasped by the user, the CPU 110 transitions the processing to step S365. When the HMD 11 is not grasped by the user, the CPU 110 transitions the processing to step S385.

In step S365, the CPU 110 waits for the value of the acceleration sensor 41 to be stable. When the value of the acceleration sensor 41 is stable, it can be determined that the HMD 11 is no longer grasped by the user. In step S370, the CPU 110 acquires a mounting angle θB of the HMD 11 by using the gyro sensor 42.

In step S375, the CPU 110 determines whether the mounting angle θ of the HMD 11 changes to be equal to or greater than a threshold value. Specifically, the CPU 110 determines whether |θA−θB| is equal to or greater than the threshold value. When |θA−θB| is equal to or greater than the threshold value, the CPU 110 transitions the processing to step S380. When |θA−θB| is less than the threshold value, the CPU 110 transitions the processing to step S385.

In step S380, the CPU 110 switches the flag F1 to 0 when the flag F1 is 1, and switches the flag F1 to 1 when the flag F1 is 0. In step S385, the CPU 110 determines whether the flag F1 is 1. When the flag F1 is 1, the CPU 110 transitions the processing to step S390, and determines that the mounting state of the HMD 11 is the first state. On the other hand, when the flag F1 is 0, the CPU 110 transitions the processing to step S395, and determines that the mounting state of the HMD 11 is not the first state.

According to the second exemplary embodiment described above, the CPU 110 detects a vibration when the HMD 11 is picked up by using the acceleration sensor 41, and measures the mounting angle θ of the HMD 11 before and after the detection of the vibration by using the gyro sensor 42. When the mounting angle changes to be equal to or greater than a predetermined angle, the CPU 110 can easily determine that a mounting state changes from a state that is the first state to a state that is not the first state or changes from a state that is not the first state to a state that is the first state.

Third Exemplary Embodiment

Figure 12:
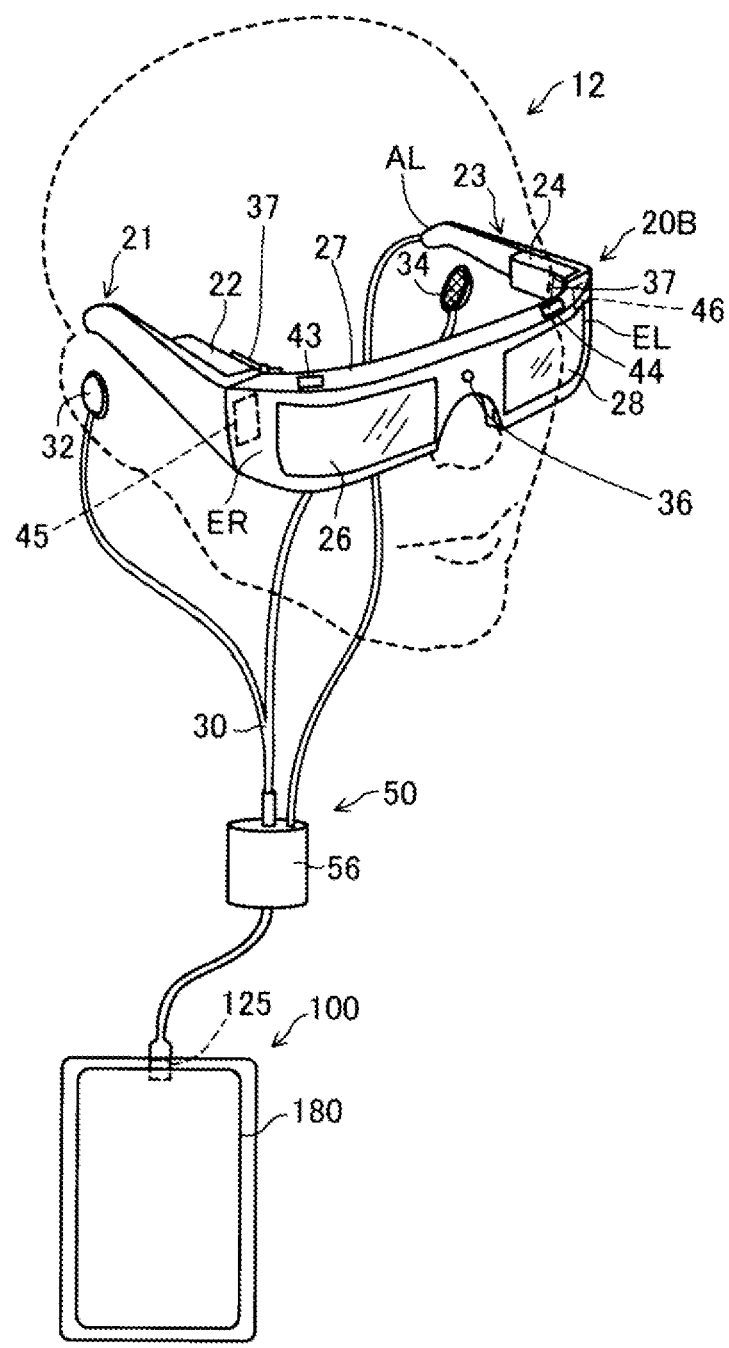
FIG. 12 is an explanatory diagram illustrating a head-mounted display apparatus according to a third exemplary embodiment.

FIG. 12 is an explanatory diagram illustrating a head-mounted display apparatus 12 (hereinafter referred to as an "HMD 12") according to a third exemplary embodiment. The HMD 10 in the first exemplary embodiment and the HMD 12 in the third exemplary embodiment are different in a sensor for detecting a mounting state, but other configurations are the same. Hereinafter, a sensor for detecting a mounting state and a control flow using the sensor will be described.

The HMD 12 includes contact sensors 43 and 44 in the front frame 27, and a camera 36 is provided in a coupling portion of the right light-guiding plate 26 and the left light-guiding plate 28 of the front frame 27. The camera 36 is a digital camera including an imaging element such as a charge-coupled device (CCD) and a complementary metal oxide semiconductor (CMOS), an imaging lens, and the like. The camera 36 is a monocular camera, but a stereo camera may be adopted. The camera 36 is configured to capture an image of at least part of an outside scenery (real space) in a front direction of the HMD 12, i.e., in a direction of the field of view in a mounting state of the image display unit 20. In the example in FIG. 10, the contact sensors 43 and 44 are provided in the front frame 27, but may be provided in the temples 21 and 23. Further, when the camera 36 can also capture the front direction of the HMD 12, the camera 36 may be provided in a place other than the coupling portion of the right light-guiding plate 26 and the left light-guiding plate 28 of the front frame 27.

Figure 13:
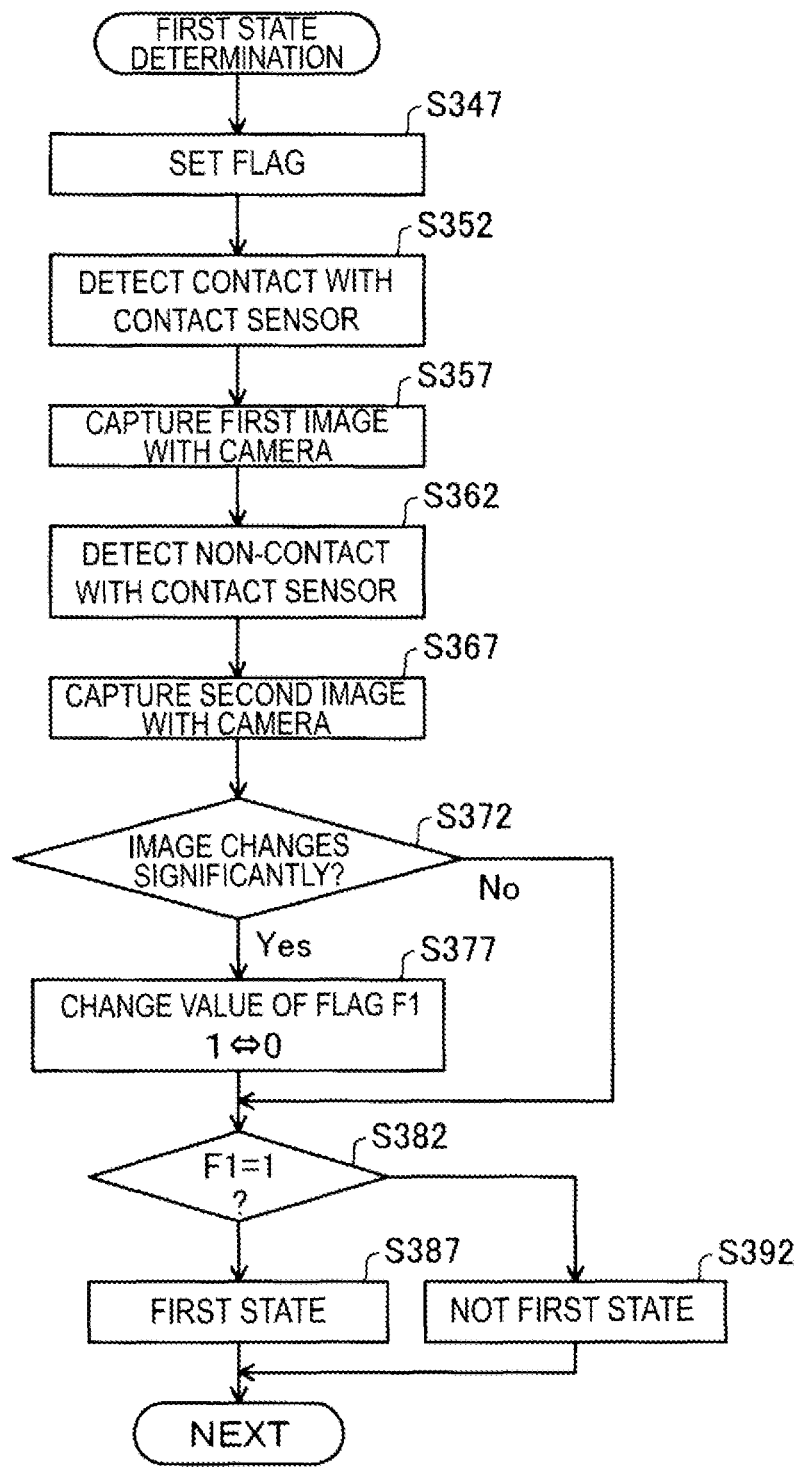
FIG. 13 is an example of a first state determination flowchart performed by the CPU in step S300 in FIG. 5 in the third exemplary embodiment.

FIG. 13 is an example of a first state determination flowchart performed by the CPU 110 in step S300 in FIG. 5 in the third exemplary embodiment. When the CPU 110 detects a contact of the user with the contact sensors 43 and 44 in step S352, the CPU 110 transitions the processing to step S357 and captures a first image by using the camera 36. When the CPU 110 detects no contact of the user with the contact sensors 43 and 44 in step S362, the CPU 110 transitions the processing to step S367 and captures a second image by using the camera 36.

In step S372, the CPU 110 compares the first image with the second image, and determines whether the image has changed significantly. For example, when a shape that is present in the first image is not present in the second image, when a shape that is not present in the first image is present in the second image, or when the first image and the second image have different hues, the CPU 110 determines that the image has changed significantly. In step S372, when the CPU 110 determines that the image has changed significantly, the CPU 110 transitions the processing to step S377, and, when the CPU 110 determines that it cannot be said that the image has changed significantly, the CPU 110 terminates the processing.

In step S377, similarly to step S380 in FIG. 11 in the second exemplary embodiment, when the mounting state before the user contacts the contact sensors 43 and 44 is the first state, the CPU 110 changes the first state to a state that is not the first state, and, when the mounting state before the user contacts the contact sensors 43 and 44 is not the first state, the CPU 110 changes the state to a state that is the first state.

According to the third exemplary embodiment described above, the CPU 110 detects whether the HMD 12 is touched by the user by using the contact sensors 43 and 44, and acquires an image of the HMD 12 before and after the contact by using the camera 36. When the two images change significantly, the CPU 110 can easily determine that a mounting state changes from a state that is the first state to a state that is not the first state or changes from a state that is not the first state to a state that is the first state.

The acceleration sensor 41 and the gyro sensor 42 are used in the second exemplary embodiment described above, and the contact sensors 43 and 44 and the camera 36 are used in the third exemplary embodiment. However, the acceleration sensor 41 and the camera 36 may be combined to determine a change in a mounting state, and the contact sensors 43 and 44 and the gyro sensor 42 may be combined to determine a change in a mounting state.

Fourth Exemplary Embodiment

Figure 14:
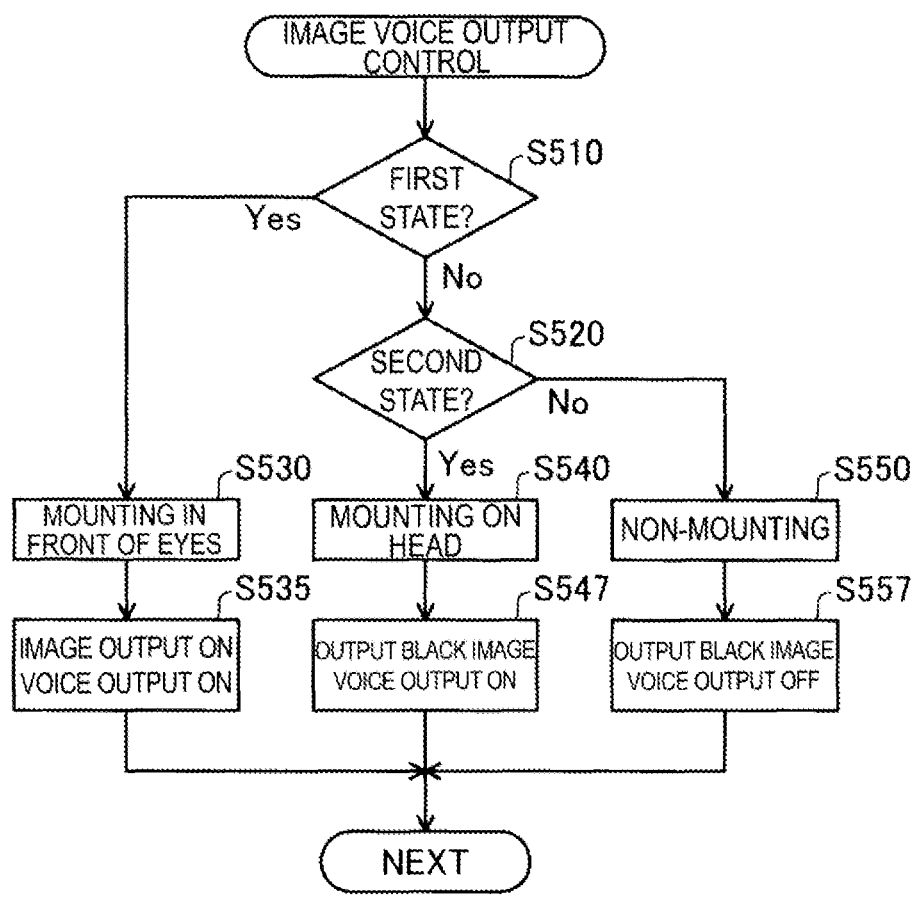
FIG. 14 is an image sound output control flowchart illustrating step S500 in FIG. 5 in a fourth exemplary embodiment.

FIG. 14 is an image sound output control flowchart illustrating step S500 in FIG. 5 in a fourth exemplary embodiment. The image sound output control flowchart illustrated in FIG. 14 is different from the image sound output control flowchart illustrated in FIG. 8 in that the image sound output control flowchart illustrated in FIG. 14 includes steps S545 and S555 instead of steps S540 and S550.

In steps S540 and S550 in FIG. 8, the CPU 110 causes the image sound output control unit 170 to turn OFF an output of an image from the image output unit 140 to the image display unit 20 of the HMD 10. In contrast, in steps S545 and S555, the CPU 110 outputs a black image from the image output unit 140 to the HMD 10. When an output of an image from the image output unit 140 to the image display unit 20 of the HMD 10 is turned OFF, there is a possibility that the CPU 110 cannot recognize the HMD 10 as an external display, but when a black image is output, there can be a lower possibility that the CPU 110 cannot recognize the HMD 10 as an external display. Further, the power consumption of the organic EL can be suppressed.

In the flowcharts illustrated in FIGS. 8 and 14, the CPU 110 first determines whether a state is the first state, and, when the state is not the first state, the CPU 110 determines whether the state is the second state. However, the CPU 110 may first determine whether a state is the second state, and, when the state is the second state, the CPU 110 may determine whether the state is the first state.

Fifth Exemplary Embodiment

Figure 15:
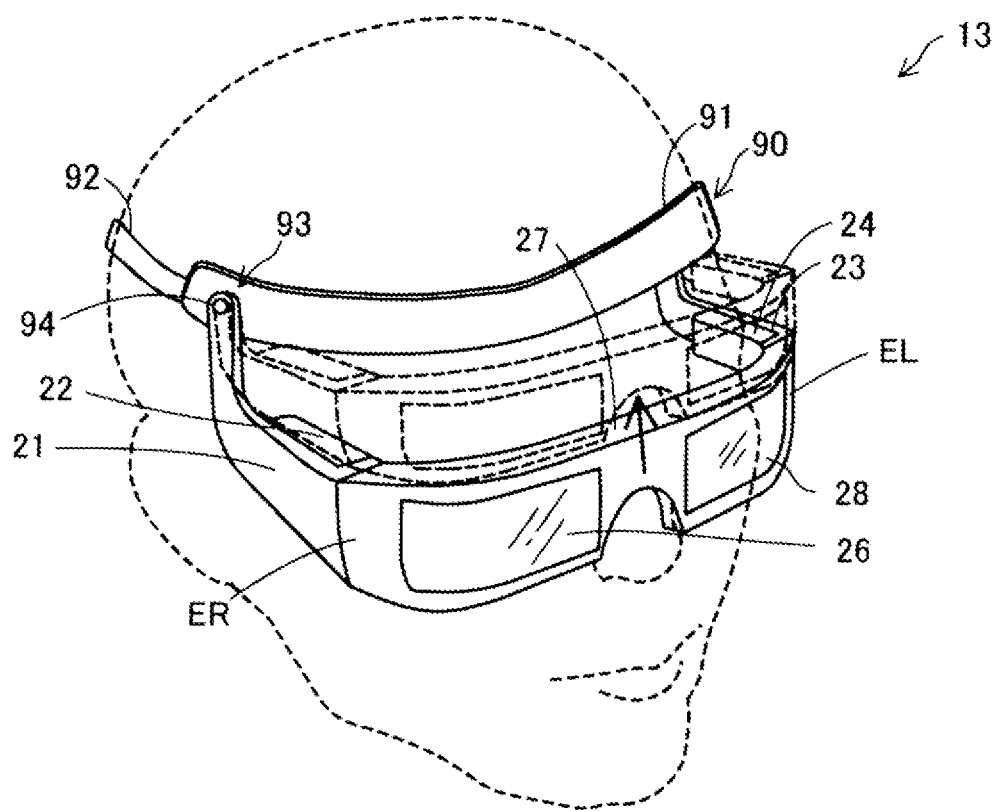
FIG. 15 is an explanatory diagram illustrating a head-mounted display apparatus according to a fifth exemplary embodiment.

In the exemplary embodiments described above, the CPU 110 determines whether a state is the first state by using the nose pad sensors 39 and 40, but the CPU 110 may determine whether a state is the first state by using a sensor other than the nose pad sensors 39 and 40. FIG. 15 is an explanatory diagram illustrating a head-mounted display apparatus 13 (hereinafter also referred to as an "HMD 13") according to a fifth exemplary embodiment. In FIG. 15, illustration of the earphones 32 and 33, the headset 30, the coupling cable 50, and the control device 100 is omitted. The HMD 12 is mounted on the head of the user by using a mounting band 90. The mounting band 90 includes a mounting base portion 91 and a belt 92 coupled to the mounting base portion 91. The mounting base portion 91 has a curved shape that matches a shape of a front head of a person. The belt 92 is mounted around the head of the user. The ends of the right holding portion 21 and the left holding portion 23 are coupled to a hinge portion 93 that couples the mounting base portion 91 and the belt 92. With this configuration, the HMD 12 can flip up the image display unit 20 about the hinge portion 93, as indicated by a broken line in FIG. 15. A state where the image display unit 20 is not flipped up is a first state. Whether or not the image display unit 20 is flipped up can be determined by, for example, providing, in the hinge portion 93, a sensor capable of detecting an angle formed by the mounting base portion 91 and the right holding portion 21 or the left holding portion 23, and using the angle detected by a sensor 94. Mounting of the image display unit 20 of the HMD 12 in a vertical direction of the head can be detected.

In FIG. 15, the hinge portion 93 and the sensor 94 are provided in the ends of the right holding portion 21 and the left holding portion 23. However, a hinge portion may be provided around above the eyes of the user to achieve flip-up of the image display unit 20. In this case, a magnetic sensor, for example, may be used as the sensor. When a magnetic sensor is provided in two places with a flip-up angle of 30° and 90°, a position of the image display unit 20 can be detected in two stages.

FIG. 16 is an explanatory diagram illustrating a relationship between a mounting state of the HMD in the fifth exemplary embodiment and ON/OFF of display of an image and a sound output of the HMD. For example, when a flip-up angle of the image display unit 20 is from 0° to 45°, the CPU 110 turns ON display of an image in the image display unit 20. The user can view the front without passing through the image display unit 20 by making the line of sight to the front, and the user can also glance at the image of the image display unit 20 by making the line of sight upward. Note that the CPU 110 may display an image only in a lower portion of the image display unit 20 when a flip-up angle of the image display unit 20 is from 15° to 45°. An image may be displayed only in a region from the lower portion of the image display unit 20 according to a flip-up angle of the image display unit 20. Further, when a flip-up angle of the image display unit 20 exceeds 45°, the CPU 110 turns OFF display of an image in the image display unit 20. Note that an optical sensor, a proximity sensor, and a potentiometer can be used as the sensor in addition to the magnetic sensor.

In FIG. 15, an example in which the right holding portion 21, the left holding portion 23, and the front frame 27 are flipped up is indicated, but a configuration in which the front frame 27 is flipped up without flipping up the right holding portion 21 and the left holding portion 23 may be adopted. In this case, the right display unit 22 and the left display unit 24 may be provided in the front frame 27 instead of the right holding portion 21 and the left holding portion 23.

The present disclosure is not limited to the embodiments described above, and may be implemented in various aspects without departing from the spirits of the disclosure. For example, the present disclosure may be achieved through the following aspects. Appropriate replacements or combinations may be made to the technical features in the above-described embodiments which correspond to the technical features in the aspects described below to solve some or all of the problems of the disclosure or to achieve some or all of the advantageous effects of the disclosure. Additionally, when the technical features are not described herein as essential technical features, such technical features may be deleted appropriately.

(1) According to an aspect of the present disclosure, a head-mounted display apparatus is provided. The head-mounted display apparatus includes an image display unit configured to display an image, a sound output unit configured to output a sound, a mounting state determination unit configured to determine a mounting state of the head-mounted display apparatus, and an image sound output control unit configured to turn ON/OFF display of an image by the image display unit, and turn ON/OFF an output of a sound by the sound output unit, based on the mounting state, where the mounting state determination unit determines whether the mounting state is a first state where the head-mounted display apparatus is mounted in a position in which an image is visually recognizable, and determines whether the mounting state is a second state where the head-mounted display apparatus is mounted on a head, and the image sound output control unit is configured to turn ON display of an image and an output of a sound when the mounting state is the first state, turn OFF display of an image and turn ON an output of a sound when the mounting state is not the first state and is the second state, and turn OFF display of an image and an output of a sound when the mounting state is not the first state and is not the second state. According to this aspect, the mounting state determination unit easily distinguishes between the first state where the head-mounted display apparatus is mounted in a first position in which an image is visually recognizable and the second state where the head-mounted display apparatus is mounted on a head. In the second state, the image display unit does not display an image, and thus power saving can be achieved.

(2) In the above-described aspect, the mounting state determination unit may determine a mounting state of the head-mounted display apparatus in a vertical direction of a head. According to this aspect, it is possible to determine whether the head-mounted display apparatus is flipped up and mounted.

(3) In the above-described aspect, the head-mounted display apparatus may further include a nose pad sensor configured to detect whether a nose is in contact with the head-mounted display apparatus, where the mounting state determination unit may determine that a state is the first state when the head-mounted display apparatus is in contact with a nose, and determine that a state is not the first state when the head-mounted display apparatus is not in contact with a nose. According to this aspect, it is possible to easily determine whether a state is the first state.

(4) In the above-described aspect, the head-mounted display apparatus may further include a front frame configured to support the image display unit, temples provided so as to sandwich the frame, a hinge configured to couple the front frame and the temples in an openable and closable manner and a pressure sensor configured to detect pressure when the hinge is open, where the mounting state determination unit may determine whether the mounting state is the second state or is not the second state by using pressure detected by the pressure sensor. According to this aspect, it is possible to easily determine whether the mounting state is the second state or is not the second state by using a change in pressure detected by the pressure sensor.

(5) In the above-described aspect, the head-mounted display apparatus may further include an acceleration sensor and a gyro sensor, where the mounting state determination unit may detect a vibration when the head-mounted display apparatus is picked up by using the acceleration sensor, measure a mounting angle of the head-mounted display apparatus before and after the detection of the vibration by using the gyro sensor, and determine whether the mounting state is the first state or is not the first state by using a change in the mounting angle. According to this aspect, it is possible to easily determine whether the mounting state is the first state or is not the first state by using the acceleration sensor and the gyro sensor.

(6) In the above-described aspect, the head-mounted display apparatus may further include a camera, where the mounting state determination unit may detect a vibration when the head-mounted display apparatus is picked up by using the acceleration sensor, acquire an image of the camera before and after the head-mounted display apparatus is picked up, and determine whether the mounting state is the first state or is not the first state by using a change in the image of the camera. According to this aspect, it is possible to easily determine whether the mounting stat is the first state or is not the first state by using a change in an image of the camera before and after the head-mounted display apparatus is picked up.

(7) In the above-described aspect, the head-mounted display apparatus may further include a supply device configured to supply an image and a sound to the head-mounted display apparatus separately from the head-mounted display apparatus, where the image display unit may include an organic EL, and the supply device may supply a black image to the head-mounted display apparatus when a state is not the first state. According to this aspect, the supply device supplies a black image to the head-mounted display apparatus when a state is not the first state, and thus the head-mounted display apparatus can be recognized as an external display.

(8) According to an aspect of the present disclosure, a power saving control program for a head-mounted display apparatus is provided. The power saving control program for a head-mounted display apparatus causing a control device of the head-mounted display apparatus to achieve a function of displaying an image on an image display unit, a function of outputting a sound to a sound output unit, a determination function of determining a mounting state of the head-mounted display apparatus, and an output control function of turning ON/OFF display of an image and turning ON/OFF an output of a sound, based on the mounting state, where the determination function includes a function of determining whether the mounting state is a first state where the head-mounted display apparatus is mounted in a position in which an image is visually recognizable, and determining whether the mounting state is a second state where the head-mounted display apparatus is mounted on a head, and the output control function includes a function of turning ON display of an image and an output of a sound when the mounting state is the first state, turning OFF display of an image and turning ON an output of a sound when the mounting state is not the first state and is the second state, and turning OFF display of an image and an output of a sound when the mounting state is not the first state and is not the second state. According to this aspect, the mounting state determination unit easily distinguishes between the first state where the head-mounted display apparatus is mounted in a first position in which an image is visually recognizable and the second state where the head-mounted display apparatus is mounted on a head, and does not output an image in the second state. Thus, power saving can be achieved.

The present disclosure may be embodied in various forms other than the head-mounted display apparatus. For example, the present disclosure can be achieved in exemplary embodiments such as a power saving control program for a head-mounted display apparatus and a non-temporary recording medium recording the power saving control program.

What is claimed is:

1. A head-mounted display apparatus, comprising:
   an image display unit configured to display an image;
   a sound output unit configured to output a sound;
   a front frame configured to support the image display unit;
   a contact sensor disposed in the front frame;
   a camera disposed in the front frame;
   a mounting state determination unit configured to determine a mounting state of the head-mounted display apparatus; and
   an image sound output control unit configured to turn ON/OFF display of an image by the image display unit, and turn ON/OFF an output of a sound by the sound output unit, based on the mounting state, wherein
   the mounting state determination unit determines whether the mounting state is a first state where the head-mounted display apparatus is mounted in a position in which an image is visually recognizable, and determines whether the mounting state is a second state where the head-mounted display apparatus is mounted on a head,
   the mounting state determination unit acquires a first image of an outside scenery by using the camera in response to detecting a contact of a user with the contact sensor and then acquires a second image of the outside scenery by using the camera in response to detecting the user is no longer in contact with the contact sensor, and determines whether the mounting state is the first state or is not the first state by comparing the first image with the second image, wherein the mounting state determination unit determines that the mounting state is the first state in response to determining a visually recognizable change between the first image and the second image in a case where the head-mounted display is initially turned ON, and
   the image sound output control unit is configured to
   turn ON display of an image and an output of a sound when the mounting state is the first state,
   turn OFF display of an image and turn ON an output of a sound when the mounting state is not the first state and is the second state, and
   turn OFF display of an image and an output of a sound when the mounting state is not the first state and is not the second state.

2. The head-mounted display apparatus according to claim 1, wherein
   the mounting state determination unit determines a mounting state of the head-mounted display apparatus in a vertical direction of a head.

3. The head-mounted display apparatus according to claim 1, further comprising:
   temples provided so as to sandwich the frame;
   a hinge configured to couple the front frame and the temples in an openable and closable manner; and
   a pressure sensor configured to detect pressure when the hinge is open, wherein
   the mounting state determination unit determines whether the mounting state is the second state or is not the second state by using pressure detected by the pressure sensor, wherein the mounting state determination unit determines that the mounting state is in the second state as the pressure sensor detects an increase in the pressure.

4. The head-mounted display apparatus according to claim 1, comprising
   an acceleration sensor and a gyro sensor, wherein
   the mounting state determination unit detects, by using the acceleration sensor, a vibration when the head-mounted display apparatus is picked up, measures, by using the gyro sensor, a mounting angle of the head-mounted display apparatus before and after the detection of the vibration, and determines whether the mounting state is the first state or is not the first state by using a change in the mounting angle.

5. The head-mounted display apparatus according to claim 4,
   wherein the mounting state determination unit detects, by using the acceleration sensor, a vibration when the head-mounted display apparatus is picked up, acquires an image of the camera before and after the head-mounted display apparatus is picked up, and determines whether the mounting state is the first state or is not the first state by using a change of the image of the camera.

6. The head-mounted display apparatus according to claim 1, comprising, separately from the head-mounted display apparatus,
a supply device configured to supply an image and a sound to the head-mounted display apparatus, wherein the image display unit includes an organic EL, and
the supply device supplies a black image to the head-mounted display apparatus when the mounting state is not the first state.

7. A non-transitory computer readable medium storing a power saving control program for a head-mounted display apparatus with a contact sensor and a camera disposed in a front frame of the head-mount display apparatus, the program causing a control device of the head-mounted display apparatus to achieve:
a function of displaying an image on an image display unit;
a function of outputting a sound to a sound output unit;
a determination function of determining a mounting state of the head-mounted display apparatus; and
an output control function of turning ON/OFF display of an image and turning ON/OFF an output of a sound, based on the mounting state, wherein
the determination function includes a function of determining whether the mounting state is a first state where the head-mounted display apparatus is mounted in a position in which an image is visually recognizable, and determining whether the mounting state is a second state where the head-mounted display apparatus is mounted on a head,
the determination function further includes a function of acquiring a first image of an outside scenery by using the camera in response to detecting a contact of a user with the contact sensor and then acquiring a second image of the outside scenery by using the camera in response to detecting the user is no longer in contact with the contact sensor, and determining whether the mounting state is the first state or is not the first state by comparing the first image with the second image, wherein the determination function determines that the mounting state is the first state in response to determining a visually recognizable change between the first image and the second image in a case where the head-mounted display is initially turned ON, and
the output control function includes a function of
turning ON display of an image and an output of a sound when the mounting state is the first state,
turning OFF display of an image and turning ON an output of a sound when the mounting state is not the first state and is the second state, and
turning OFF display of an image and an output of a sound when the mounting state is not the first state and is not the second state.

* * * * *